United States Patent
Walters et al.

(10) Patent No.: US 6,878,538 B1
(45) Date of Patent: Apr. 12, 2005

(54) APPARATUS FOR RECEIVING AND ALIGNING A MULTIPLE ELECTRODE PAIR ARRAY AND A MULTIPLE TREATMENT CELL FOR USE IN ELECTROPORATION

(75) Inventors: Richard E. Walters, Columbia, MD (US); Benjamin R. Lane, Phoenix, MD (US); Michael S. Abbott, Baltimore, MD (US)

(73) Assignee: Cyto Pulse Sciences, Inc., Glen Burnie, MD (US)

( * ) Notice: Subject to any disclaimer, the term of this patent is extended or adjusted under 35 U.S.C. 154(b) by 0 days.

(21) Appl. No.: 10/694,344

(22) Filed: Oct. 28, 2003

(51) Int. Cl.[7] ............................................. C12M 1/42
(52) U.S. Cl. ............................... 435/285.2; 435/287.3; 435/288.4; 435/305.2; 435/305.3; 435/809; 204/403.01; 204/412; 204/400
(58) Field of Search ........................... 435/285.2, 287.3, 435/288.4, 305.2, 305.3, 809; 204/400, 403.01, 412

(56) References Cited

U.S. PATENT DOCUMENTS

| | | | | |
|---|---|---|---|---|
| 5,432,086 A | * | 7/1995 | Franzl et al. ............ | 435/286.2 |
| 6,352,853 B1 | * | 3/2002 | King et al. .............. | 435/285.2 |
| 6,376,233 B1 | * | 4/2002 | Wolf et al. .............. | 435/288.4 |
| 6,653,114 B2 | * | 11/2003 | Walters et al. ........... | 435/173.6 |
| 6,686,193 B2 | * | 2/2004 | Maher et al. ............ | 435/285.2 |
| 6,764,648 B1 | * | 7/2004 | Roach et al. ................ | 422/63 |

* cited by examiner

Primary Examiner—David A. Redding
(74) Attorney, Agent, or Firm—Marvin S. Towsend

(57) ABSTRACT

An apparatus is provided for receiving and aligning a multiple electrode pair array and a multiple well plate used in electroporation. The apparatus includes a housing which includes a bottom housing portion and a pair of side housing portions which project upward from the bottom housing portion. A pair of board-reception structures are adjacent to the inner portions of the side housing portions. Multiple well plate engaging and disengaging means, supported by the housing, are provided for engaging a multiple well plate with a multiple electrode pair array and for disengaging a multiple well plate from a multiple electrode pair array. Preferably, the multiple well plate engaging and disengaging means include a multiple well plate lifting and lowering assembly. The multiple well plate lifting and lowering assembly can include lifting/lowering handles located outside the housing.

10 Claims, 11 Drawing Sheets

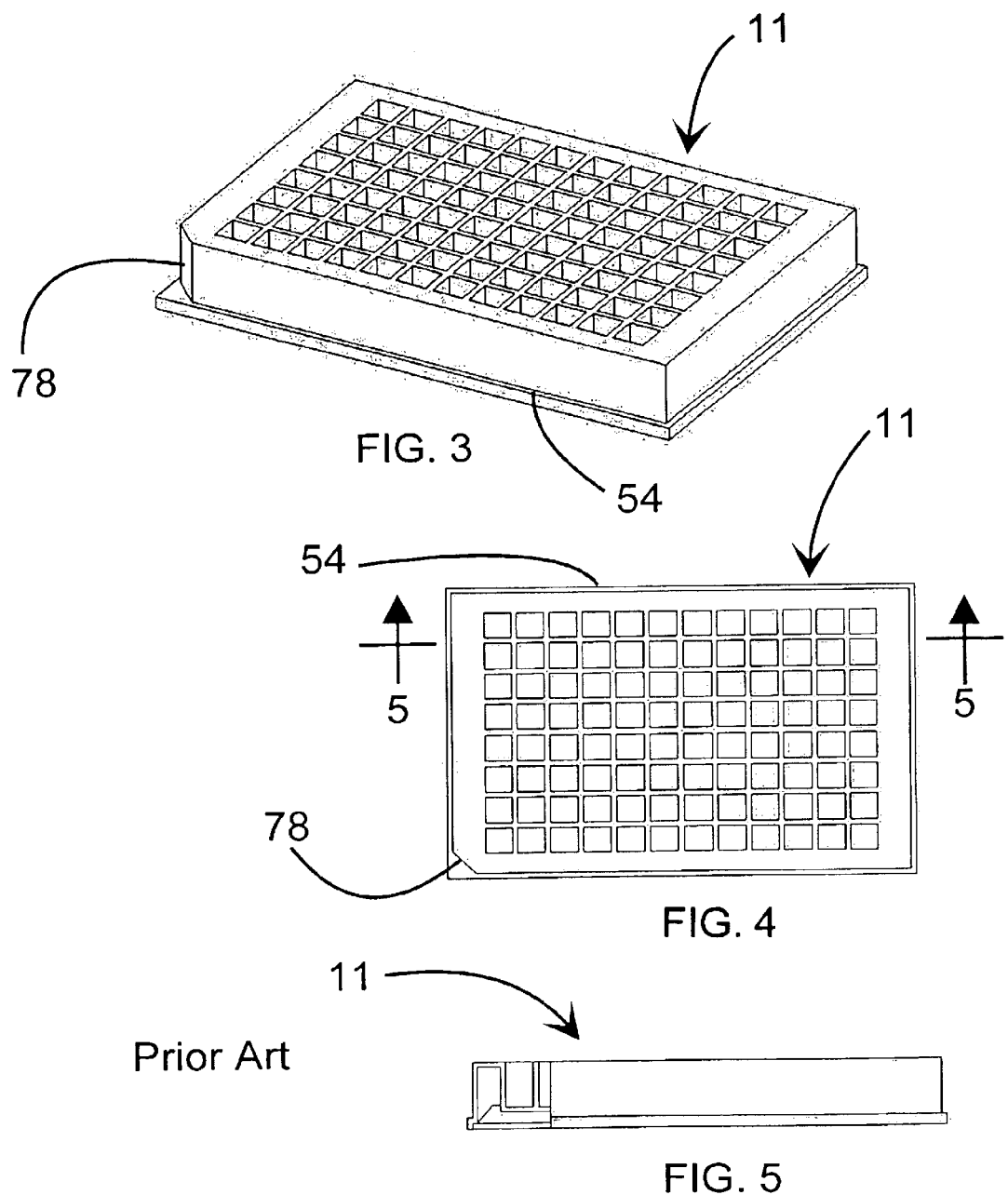

APPARATUS FOR RECEIVING AND ALIGNING A MULTIPLE ELECTRODE PAIR ARRAY AND A MULTIPLE TREATMENT CELL FOR USE IN ELECTROPORATION

CROSS-REFERENCE TO RELATED APPLICATION

The present patent application Ser. No. 10/694,345 is related to another patent application entitled IN VITRO, MULTIPLE ELECTRODE PAIR ARRAY AND MULTIPLE TREATMENT CELL APPARATUS FOR USE IN ELECTROPORATION by Walters et al, which is filed concurrently with the present application.

TECHNICAL FIELD

The present invention relates to the field of electroporation. More specifically, the present invention is especially concerned with an apparatus for receiving and aligning a multiple electrode pair array and a multiple treatment cell for use in electroporation.

BACKGROUND ART

U.S. Pat. No. 6,352,853 of King et al discloses that multi-channel electrode systems are used for high throughput introduction of exogenous molecules into cells. A multichannel electroporation apparatus includes a plurality of pairs of electrodes positioned in respective ones of a plurality of wells that hold the exogenous materials and the cells. The wells can be in standard 96-well plates, which consist of 8 rows and 12 columns of wells and have a standard size of about 8.5 (W) cm.times.12.7 cm (L), with a standard center-to-center spacing of 9.0 mm between wells.

In FIG. 5 of U.S. Pat. No. 6,352,853, there is a disclosure of a 384 well multiple well plate and 384 electrode pairs for fitting into the respective 383 wells. It certainly may be a daunting task to properly align the 384 electrode pairs with the 384 wells and to place the respective 384 electrode pairs in proper registration with the respective 384 wells. In this respect, it would be desirable if an apparatus were provided to properly align and register a multiple electrode array with a multiple well plate.

As described in the above-mentioned patent application Ser. No. 10/694,345 entitled IN VITRO, MULTIPLE ELECTRODE PAIR ARRAY AND MULTIPLE TREATMENT CELL APPARATUS FOR USE IN ELECTROPORATION by Walters et al, the amount of frictional resistance to overcome to fit a 96 electrode pair matrix array into a conventional 96 well multiple well plate can be quite substantial. In this respect, it would be desirable if an apparatus were provided which facilitates overcoming the frictional resistance for fitting a 96 electrode pair matrix array into a conventional 96 well multiple well plate. More generally, it would be desirable if an apparatus were provided which facilitates overcoming the frictional resistance for fitting a multiple electrode pair matrix array into a conventional multiple well plate.

Conversely, there is a substantial amount of frictional resistance to overcome to remove a 96 electrode pair matrix array from a 96 well multiple well plate after it has been fitted into a 96 well multiple well plate. In this respect, it would be desirable if an apparatus were provided which facilitates overcoming the frictional resistance to remove a 96 electrode pair matrix array from a conventional 96 well plate. More generally, it would be desirable if an apparatus were provided which facilitates overcoming the frictional resistance to remove a multiple electrode pair matrix array from a conventional multiple well plate.

Each well in a standard 96 rectangular well plate has a predetermined well volume. When pairs of rectangular electrodes are placed into the wells, the predetermined volumes are reduced, thereby leaving a reduced volume for conducting electroporation of materials. To assure that the predetermined volumes are reduced to a minimum by the electrodes so that the remaining volumes available for electroporation are at a maximum, it would be desirable if pairs of rectangular electrodes were placed into the rectangular wells so that the rectangular electrodes closely fit against adjacent walls of the wells.

Thus, while the foregoing body of prior art indicates it to be well known to use multiple electrode pair arrays and multiple well plates, the prior art described above does not teach or suggest an apparatus for receiving and aligning a multiple electrode pair array and a multiple well plate for electroporation which has the following combination of desirable features: (1) properly aligns and registers a multiple electrode array with a multiple well plate; (2) facilitates overcoming the frictional resistance for fitting a 96 electrode pair matrix array into a conventional 96 well multiple well plate; (3) facilitates overcoming the frictional resistance for fitting a multiple electrode pair matrix array into a conventional multiple well plate; (4) facilitates overcoming the frictional resistance to remove a 96 electrode pair matrix array from a conventional 96 well plate; (5) facilitates overcoming the frictional resistance to remove a multiple electrode pair matrix array from a conventional multiple well plate; and (6) places pairs of rectangular electrodes into rectangular wells so that the rectangular electrodes closely fit against adjacent walls of the wells. The foregoing desired characteristics are provided by the unique apparatus for receiving and aligning a multiple electrode pair array and a multiple well plate of the present invention as will be made apparent from the following description thereof. Other advantages of the present invention over the prior art also will be rendered evident.

DISCLOSURE OF INVENTION

To achieve the foregoing and other advantages, the present invention, briefly described, provides an apparatus for receiving and aligning a multiple electrode pair array and a multiple well plate used in electroporation. The apparatus includes a housing which includes a bottom housing portion and a pair of side housing portions which project upward from the bottom housing portion. A pair of board-reception structures are adjacent to the inner portions of the side housing portions. Multiple well plate engaging and disengaging means, supported by the housing, are provided for engaging a multiple well plate with a multiple electrode pair array and for disengaging a multiple well plate from a multiple electrode pair array.

Preferably, the multiple well plate engaging and disengaging means include a multiple well plate lifting and lowering assembly. The multiple well plate lifting and lowering assembly can include lifting/lowering handles located outside the housing. An offset axle is connected to the lifting/lowering handles. The offset axle includes a driving cam portion. Tray lift rods are in contact with the driving cam portion of the offset axle. The tray lift rods are connected to the bottom housing portion by lift-rod-retainer portions. A plate lifting/lowering tray is in contact with the tray lift rods. A bottom portion of the plate lifting/lowering tray includes a plurality of transverse force-balancing ribs. The tray lift rods are for raising the plate lifting/lowering tray. Tray lowering cams are connected to a bottom portion of the plate lifting/lowering tray, for engaging the offset axle for lowering the plate lifting/lowering tray.

A pair of well-plate alignment grooves are connected to the plate lifting/lowering tray adjacent to the board-reception structures. An inside alignment surface (not shown) is contacted by a complementary outside alignment surface on an outside corner of the multiple well plate when the multiple well plate and the apparatus are in proper alignment.

Preferably, hold-down clips are supported by the housing and are actuated by movement of the plate lifting/lowering tray.

Hold-down-clip actuator arms are operated by the plate lifting/lowering tray for actuating the hold-down clips.

A lid is connected to the housing. A pair of hinges are provided for connecting the lid to the housing.

Preferably, a socket assembly is supported by the housing. The socket assembly includes electrical conductors for contacting corresponding row electrical connection members and column electrical connection members on the multiple electrode pair array.

Preferably, an adjacent electrode pair spacing gap is provided between a first electrode on one pair of electrodes and a second electrode on an adjacent pair of electrodes, such that an inside wall of the multiple well plate is received in the adjacent electrode pair spacing gap. More specifically, the respective inside walls of the multiple well plate are received in the respective adjacent electrode pair spacing gaps by relatively tight friction fits. As a result, the respective first electrodes and the respective second electrodes fit tightly against the respective inside walls, thereby leaving a maximum amount of space for sample reception and electroporation in the respective wells of the multiple well plate.

It is, therefore, an object of the present invention is to provide an apparatus for receiving and aligning a multiple electrode pair array and a multiple well plate which properly aligns and registers a multiple electrode array with a multiple well plate.

Still another object of the present invention is to provide an apparatus for receiving and aligning a multiple electrode pair array and a multiple well plate that facilitates overcoming the frictional resistance for fitting a 96 electrode pair matrix array into a conventional 96 well multiple well plate.

Yet another object of the present invention is to provide an apparatus for receiving and aligning a multiple electrode pair array and a multiple well plate which facilitates overcoming the frictional resistance for fitting a multiple electrode pair matrix array into a conventional multiple well plate.

Even another object of the present invention is to provide an apparatus for receiving and aligning a multiple electrode pair array and a multiple well plate that facilitates overcoming the frictional resistance to remove a 96 electrode pair matrix array from a conventional 96 well plate.

Still a further object of the present invention is to provide an apparatus for receiving and aligning a multiple electrode pair array and a multiple well plate which facilitates overcoming the frictional resistance to remove a multiple electrode pair matrix array from a conventional multiple well plate.

Yet another object of the present invention is to provide an apparatus for receiving and aligning a multiple electrode pair array and a multiple well plate that places pairs of rectangular electrodes into rectangular wells so that the rectangular electrodes closely fit against adjacent walls of the wells.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawing wherein:

FIG. 3 is a top perspective view of the PRIOR ART standard 96 rectangular well plate shown is FIG. 1.

FIG. 4 is a top view of the PRIOR ART standard 96 rectangular well plate shown in FIG. 3.

FIG. 5 is a partial cross-sectional view of the standard 96 rectangular well plate shown in FIG. 4 taken along line 5—5 thereof.

MODE FOR CARRYING OUT THE INVENTION

With reference to the drawings, an apparatus for receiving and aligning a multiple electrode pair array and a multiple treatment cell used in electroporation 40 embodying the principles and concepts of the present invention will be described.

Filed concurrently herewith is a patent application Ser. No. 10/694,345 entitled IN VITRO, MULTIPLE ELECTRODE PAIR ARRAY AND MULTIPLE TREATMENT CELL APPARATUS FOR USE IN ELECTROPORATION by Walters et al which sets forth a multiple electrode pair array apparatus having a two-dimensional matrix array of electrode conductors that is used with a conventional multiple well plate. In this respect, that patent application is incorporated herein by reference.

Figure 13:
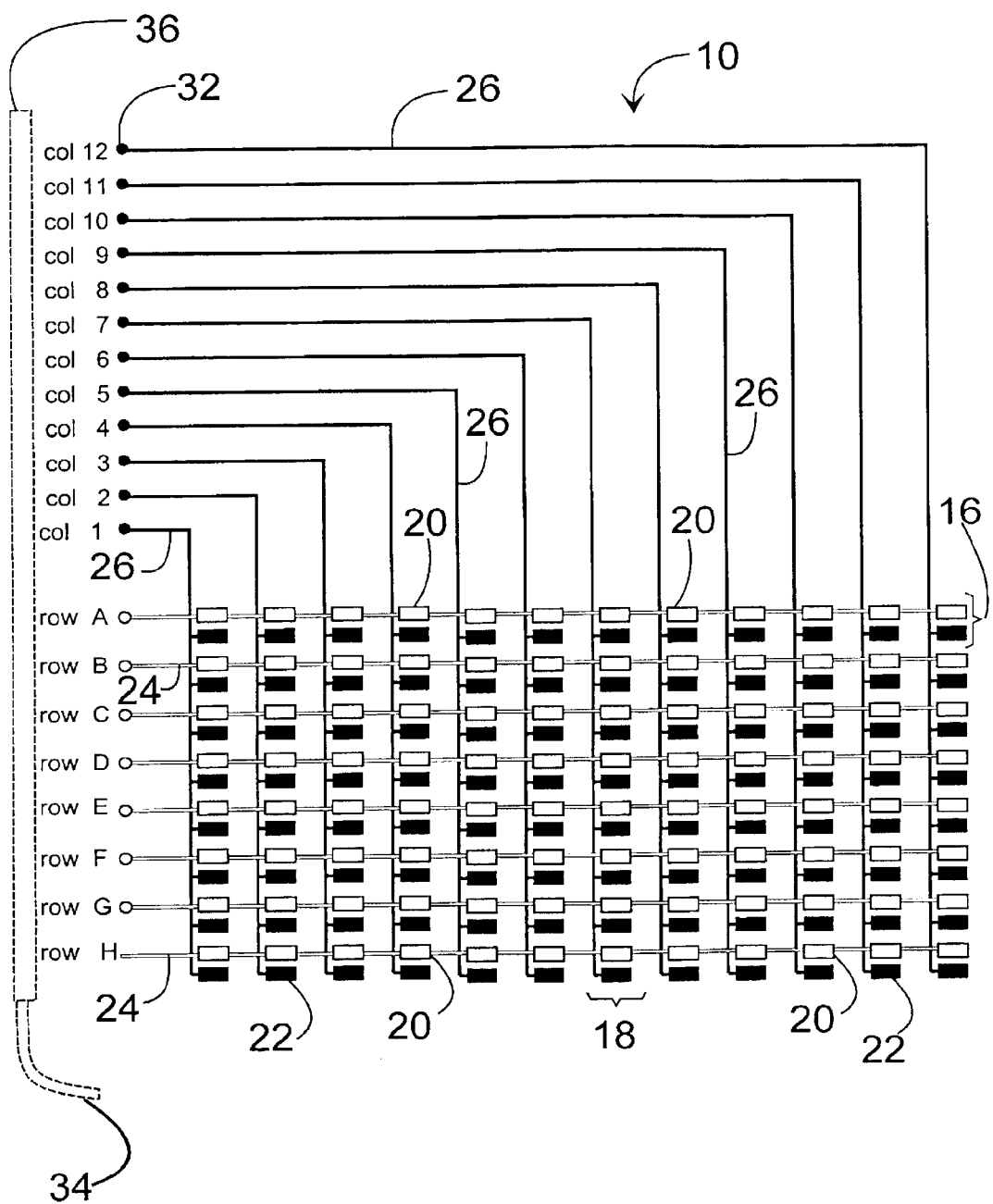
FIG. 13 is a schematic diagram of a two-dimensional matrix array of 20 matrix conductors (8 row conductors and 12 column conductors) to connect with 96 pairs of electrodes in a matrix array of electrodes (having 8 rows of electrode pairs and 12 columns of electrode pairs) for a 96 well plate.

In summary, with respect to the multiple electrode pair array 10, and with reference to FIG. 13 herein, the multiple electrode pair array apparatus 10 has a two-dimensional matrix array of electrode conductors and includes the following. There are electrode pairs at each two-dimensional matrix location. The matrix of electrode pairs has R rows 16 and C columns 18. Each electrode pair has a first electrode 20 electrically connected to a row conductor 24 and a second electrode 22 connected to a column conductor 26. Also, a row/column conductor cable 34 runs from the Programmable Pulse Switch Cabinet 8 (see FIG. 13), and a row/column conductor plug 36 is connected to the row/column conductor cable 34.

Each of the multiple electrode pair array apparatus 10 and the multiple well plate 11 include alignment structures to assure proper registration between the multiple electrode pair array apparatus 10 of the invention and the multiple well plate 11 when the multiple electrode pair array apparatus 10 is connected to the multiple well plate 11. The respective alignment structures assure that there is a one-to-one correspondence between the respective locations of the pairs of electrodes in the two-dimensional matrix array electrode pairs and the locations of the wells in the two-dimensional matrix array of wells in the multiple well plate 11.

Figure 10:
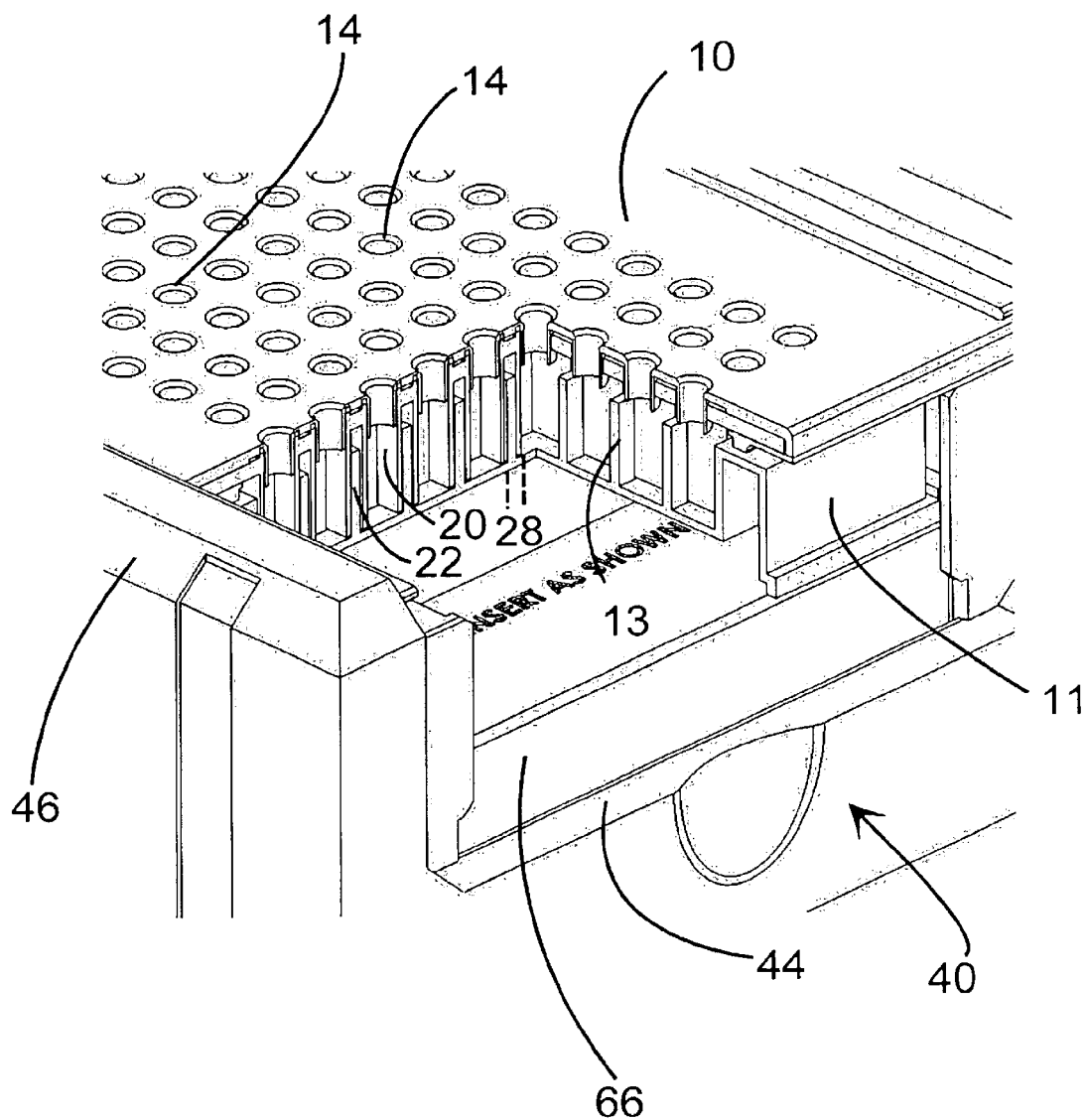
FIG. 10 is a partially enlarged view of the broken away portion of FIG. 9.

As shown in FIG. 10, adjacent electrode pair spacing gap 28 is provided between a first electrode 20 on one pair of electrodes and a second electrode 22 on an adjacent pair of electrodes, such that an inside wall 13 of the multiple well plate 11 is received in the adjacent electrode pair spacing gap 28. More specifically, the respective inside walls 13 of the multiple well plate 11 are received in the respective adjacent electrode pair spacing gaps 28 by relatively tight friction fits. As a result, the respective first electrodes 20 and the respective second electrodes 22 fit tightly against the respective inside walls 13, thereby leaving a maximum amount of space for sample reception and electroporation in the respective wells of the multiple well plate 11.

The amount of frictional resistance needed to be overcome in order to provide a tight fit between a 96 electrode pair matrix array of the invention and a conventional 96 well multiple well plate 11 can be quite substantial. The tight fit permits the respective electrode pairs in the electrode pair matrix array to provide uniform electric fields in the respective wells and to prevent material from getting behind the respective electrodes between the respective electrodes and the inside walls 13 of the multiple well plate 11.

Conversely, there is a substantial amount of frictional resistance to overcome to remove a 96 electrode pair matrix array of the invention that has-been fitted into a 96 well multiple well plate 11.

As shown in FIG. 10, preferably, the base member of the multiple electrode pair array 10 includes a plurality of access channels 14 which are in registration with the wells of the multiple well plate 11.

Preferably, the access channels 14 are circular in shape. For a 96 multiple electrode pair array with a two-dimensional matrix array of electrode conductors of the invention, for use with a conventional 96 well multiple well plate 11 which has rectangular wells, the access channels 14 can be 7 mm. in diameter.

Once the multiple electrode pair array apparatus 10 of the invention has been fitted into the multiple well plate 11, the contents of each respective well in the multiple well plate 11 can be modified through the respective access channels 14. Pressure pipettes can be used to add material to the respective wells, and suction pipettes can be used to remove material from the respective wells. The presence of the access channels 14 provide an additional benefit. The access channels 14 eliminate cross contamination between wells in the multiple well plate 11 that can occur if the electrode pair matrix array is inserted into the wells after the wells have been filled with liquid solution.

FIGS. 3, 4, and 5 show a number of views of a conventional 96 rectangular well multiple well plate 11 that is registerable with a 96 multiple electrode pair array with a two-dimensional matrix array of electrode conductors of the invention. In this respect, the adjacent electrode pair spacing gap 28 is approximately equal to the thickness of the inside walls 13 of the respective wells.

Figure 12:
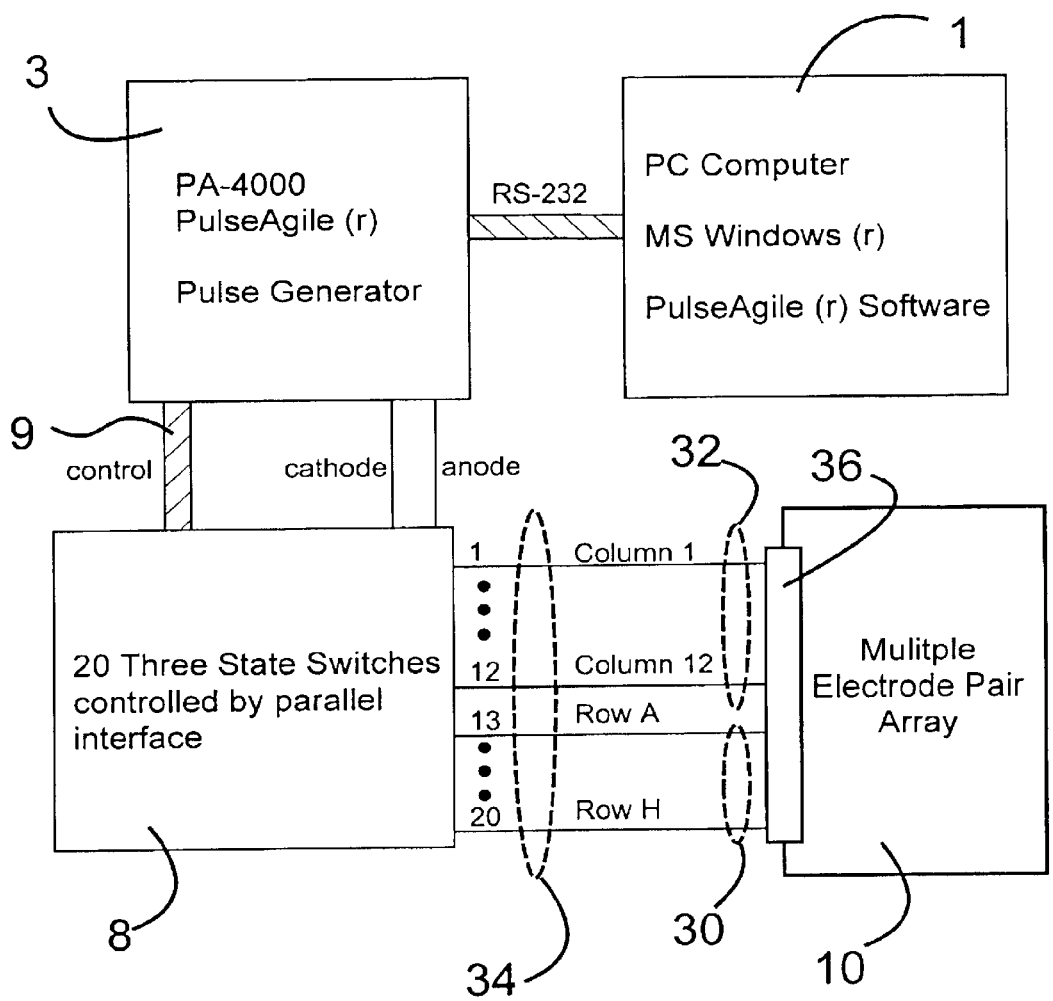
FIG. 12 is a block diagram of the overall electroporation system used to drive the multiple electrode pair array and the two-dimensional matrix array of electrode conductors disclosed in the above-mentioned patent application for IN VITRO, MULTIPLE ELECTRODE PAIR ARRAY AND MULTIPLE TREATMENT CELL APPARATUS FOR USE IN ELECTROPORATION.

FIG. 12 shows the PA-4000 electroporation system, of Cyto Pulse Sciences, Inc., Hanover, Md., USA, which is configured with the Programmable Pulse Switch 8. More disclosures about the structure and the operation of the electroporation system of Cyto Pulse Sciences, Inc. are disclosed in U.S. Pat. No. 6,010,613 of Walters et al, incorporated herein by reference and in U.S. Pat. No. 6,117,660 of Walters et al, which is incorporated herein by reference.

A control cable 9 is used to control the Programmable Pulse Switch 8. The Programmable Pulse Switch 8 has 20 output conductor lines which include eight row conductor lines A through H and which include twelve column conductor lines 1 through 12. The eight row conductor lines A through H and the twelve column conductor lines 1 through 12 from the Programmable Pulse Switch Cabinet 8 to the multiple electrode pair array apparatus 10 can be in form of a row/column conductor cable 34. The row/column conductor cable 34 can terminate at row/column conductor plug 36 which is electrically connected to the respective row and column conductor lines in the row/column conductor cable 34. The row/column conductor plug 36 can include respective conductor contact elements which form electrical connections with the respective row electrical connection members 30 and the column electrical connection members 32 of the multiple electrode pair array apparatus 10. The 20 output conductor lines are set to one and only one of three states, pulse out, pulse return, no connection.

The overall electroporation system consists of three cabinets: (1) the compatible PC 1; (2) the PA-4000 cabinet 3 which contains the control microprocessor, the Interface-Control Assembly, the High Voltage Assembly, the High Voltage Power Supply, and the low voltage power supply; and (3) the Programmable Pulse Switch Cabinet 8.

The row conductor lines A through H of the Programmable Pulse Switch Cabinet 8 are electrically connected to the respective row electrical connection members 30 of the multiple electrode pair array apparatus 10. The column conductor lines 1–12 of the Programmable Pulse Switch Cabinet 8 are electrically connected to the respective column electrical connection members 32 of the multiple electrode pair array apparatus 10.

By appropriate programming by a user, any specific electrode pair in the matrix array of 96 electrode pairs can be selected for applying an electric field therein for a selected period of time and for a selected pulse pattern.

Each of the 96 electrode pairs is located at a location identified by a row position and a column position in the two-dimensional multiple electrode pair array. To select a specific electrode pair, the corresponding row conductor 24 for the first electrode 20 of the specific electrode pair and the corresponding column conductor 26 for the second electrode 22 of the specific electrode pair are energized from signals sent from the Programmable Pulse Switch Cabinet 8. As a result, the only electrode pair energized is the specific electrode pair located at the intersection of the specific row conductor and the specific column conductor that are energized by the Programmable Pulse Switch Cabinet 8.

One embodiment of the multiple electrode pair array of the invention can be used with standard disposable rectangular well 96 well microplates such as made by Innovative Microplate, Chicopee, Mass., USA, particularly, Microplate Model S30012.

For purposes of the present invention, a multiple treatment cell and a multiple well plate are substantially equivalent.

Now, with reference to FIGS. 1 and 6–11, turning to a detailed description of the present apparatus for receiving and aligning a multiple electrode pair array and a multiple well plate 40 for electroporation, the apparatus is provided for receiving and aligning a multiple electrode pair array 10 and a multiple well plate 11 used in electroporation 40. The apparatus 40 includes a housing 42 which includes a bottom housing portion 44 and a pair of side housing portions 46 which project upward from the bottom housing portion 44. A pair of board-reception structures 48 are adjacent to the inner portions of the side housing portions 46. Multiple well plate engaging and disengaging means, supported by the housing 42, are provided for engaging a multiple well plate 11 with a multiple electrode pair array 10 and for disengaging a multiple well plate 11 from a multiple electrode pair array 10.

Preferably, the multiple well plate engaging and disengaging means include a multiple well plate lifting and lowering assembly. The multiple well plate lifting and lowering assembly can include lifting/lowering handles 56 located outside the housing 42. An offset axle 58 is connected to the lifting/lowering handles 56. The offset axle 58 includes a driving cam portion 60. Tray lift rods 62 are in contact with the driving cam portion 60 of the offset axle 58. The tray lift rods 62 are connected to the bottom housing portion 44 by lift-rod-retainer portions 64. A plate lifting/lowering tray 66 is in contact with the tray lift rods 62. A bottom portion of the plate lifting/lowering tray 66 includes a plurality of transverse force-balancing ribs 68. The tray lift rods 62 are for raising the plate lifting/lowering tray 66. Tray lowering cams 80 are connected to a bottom portion of the plate lifting/lowering tray 66, for engaging the offset axle 58 for lowering the plate lifting/lowering tray 66. The multiple well plate 11 is received on the plate lifting/lowering tray 66 and is lifted and lowered thereby.

Alternatively, the multiple well plate engaging and disengaging means can be implemented by electrical means.

A pair of well-plate alignment grooves 50 are connected to the plate lifting/lowering tray 66 adjacent to the board-reception structures 48. The well-plate alignment grooves 50 are provided for receiving complementary well-plate tongue portions 54 located on the multiple well plate 11. Inside alignment surface (not shown) is contacted by a complementary outside alignment surface 78 on an outside corner of the multiple well plate 11 when the multiple well plate 11 and the apparatus 40 are in proper alignment. The inside alignment surface can be in the form of a diagonal corner, and the outside alignment surface 78 of the multiple well plate 11 can be in the form of a complementary diagonal notch 78.

The alignment of the inside alignment surface in the apparatus for receiving and aligning a multiple electrode pair array and a multiple treatment well 40 with the outside alignment surface 78 on the multiple well plate 11 provide proper alignment of the multiple electrode pair array 10 with the multiple well plate 11. If the inside alignment surface and the outside alignment surface 78 are not in contact with each other, then the multiple electrode pair array 10 and the multiple well plate 11 cannot be in proper alignment.

Preferably, hold-down clips 70 are supported by the housing 42 and are actuated by movement of the plate lifting/lowering tray 66. The hold-down clips 70 serve to retain the multiple electrode pair array 10 on the board-reception structures 48 when the multiple well plate 11 is lifted up by the plate lifting/lowering tray 66 to engage with the pairs of electrodes in the multiple electrode pair array 10.

Hold-down-clip actuator arms 72 are operated by the plate lifting/lowering tray 66 for actuating the hold-down clips 70. Return springs (not shown) can be present to return the hold-down clips 70 to a retracted position when the plate lifting/lowering tray 66 has been lowered to its bottom position. Otherwise, the hold-down clips 70 can return to their non-hold-down positions by the force of gravity.

A lid 74 is connected to the housing 42. A pair of hinges 76 are provided for connecting the lid 74 to the housing 42.

Preferably, a socket assembly is supported by the housing 42. The socket assembly includes electrical conductors for contacting corresponding row electrical connection members 30 and column electrical connection members 32 on the multiple electrode pair array 10. The socket assembly is used for receiving a row/column conductor plug 36, whereby electrical voltages from the Programmable Pulse Switch Cabinet 8 (shown if FIG. 12, can be directed to selected pairs of electrodes in the respective wells of the multiple well plate 11. In addition, a disabling switch, e.g. interlock, (not shown) is actuated when the lid 74 is in the open position. The disabling switch is a part of a disabling circuit which disables the generation of voltages by the electroporation system when the lid 74 is open. The disablement of the voltage generation prevents a user from being subjected to electric shocks when the lid 74 is open.

In addition, the multiple electrode pair array 10 can also includes alignment pins (not shown) for receipt in complementary pin-reception alignment wells (not shown) which are located in the apparatus for receiving and aligning a multiple electrode pair array and a multiple treatment plate used in electroporation 40. The alignment pins can provide both alignment and electrical connection between the multiple electrode pair array 10 and the apparatus 40 for receiving and aligning a multiple electrode pair array and a multiple treatment plate used in electroporation.

In addition, other alignment means for the multiple electrode pair array 10 can be provided. For example, the multiple electrode pair array 10 can be provided with an alignment ridge, and the apparatus for receiving and aligning a multiple electrode pair array and a multiple treatment cell used in electroporation 40 can be provided with a complementary alignment groove to receive the alignment ridge.

To use the apparatus for receiving and aligning a multiple electrode pair array and a multiple well plate 40 of the invention, the lid 74 is lifted. The multiple electrode pair array 10 is placed upon the board-reception structures 48. Care is taken to properly align the multiple electrode pair array 10 with respect to the side housing portions 46.

Now, with the plate lifting/lowering tray 66 in the lowered position, as shown in FIGS. 1, 6, 7, and 8, the multiple well plate 11 is slid onto the plate lifting/lowering tray 66. More specifically, the multiple well plate 11 is oriented so that the outside alignment surface 78 on the multiple well plate 11 will engage with the inside alignment surface on the inside of the housing 42 of the apparatus 40. In addition, the well-plate tongue portions 54 are guided into the well-plate alignment grooves 50 projecting up from the plate lifting/lowering tray 66. Then, the multiple well plate 11 is moved into the apparatus 40. When the outside alignment surface 78 of the multiple well plate 11 contacts the inside alignment surface on the housing 42, the multiple electrode pair array 10 and the multiple well plate 11 are in proper registration. That is, the respective pairs of electrodes in the multiple electrode pair array 10 are in registration with the corresponding wells in the multiple well plate 11.

Figure 11:
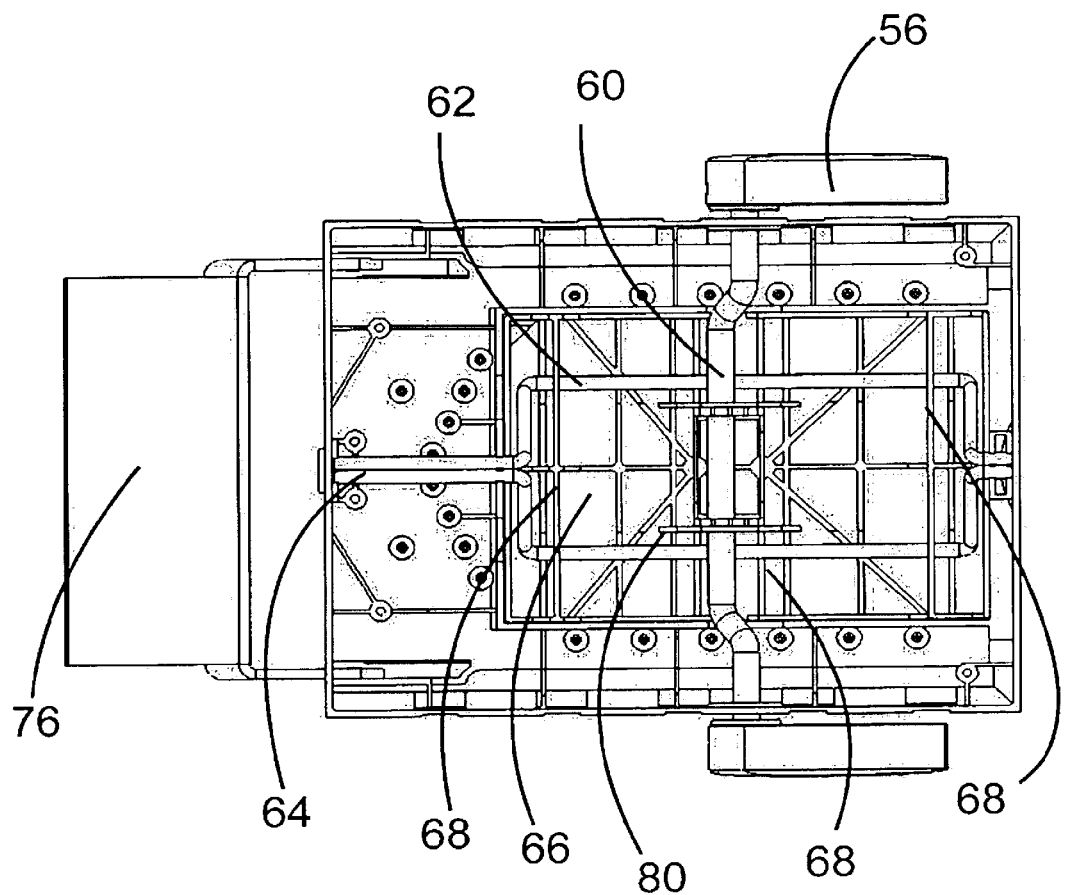
FIG. 11 is a bottom view of a multiple well plate lifting and lowering assembly that is housed inside the embodiment of the invention shown in FIGS. 1 and 6–10.

Then, as shown in FIG. 11, the lifting/lowering handles 56 are grasped and rotated in a clockwise direction. When this is done, the offset axle 58 causes the driving cam portion 60 to push up on the tray lift rods 62 and the force-balancing ribs 68 on the bottom of the plate lifting/lowering tray 66. As a result, the plate lifting/lowering tray 66 moves upward toward the multiple electrode pair array 10 causing the multiple well plate 11 supported thereon to also move upward toward the multiple electrode pair array 10. Simultaneously, the upwardly moving plate lifting/lowering tray 66 actuates the hold-down-clip actuator arms 72, thereby causing the hold-down clips 70 to move out from the side housing portions 46 to be located over top surfaces of the multiple electrode pair array 10.

Figure 1:
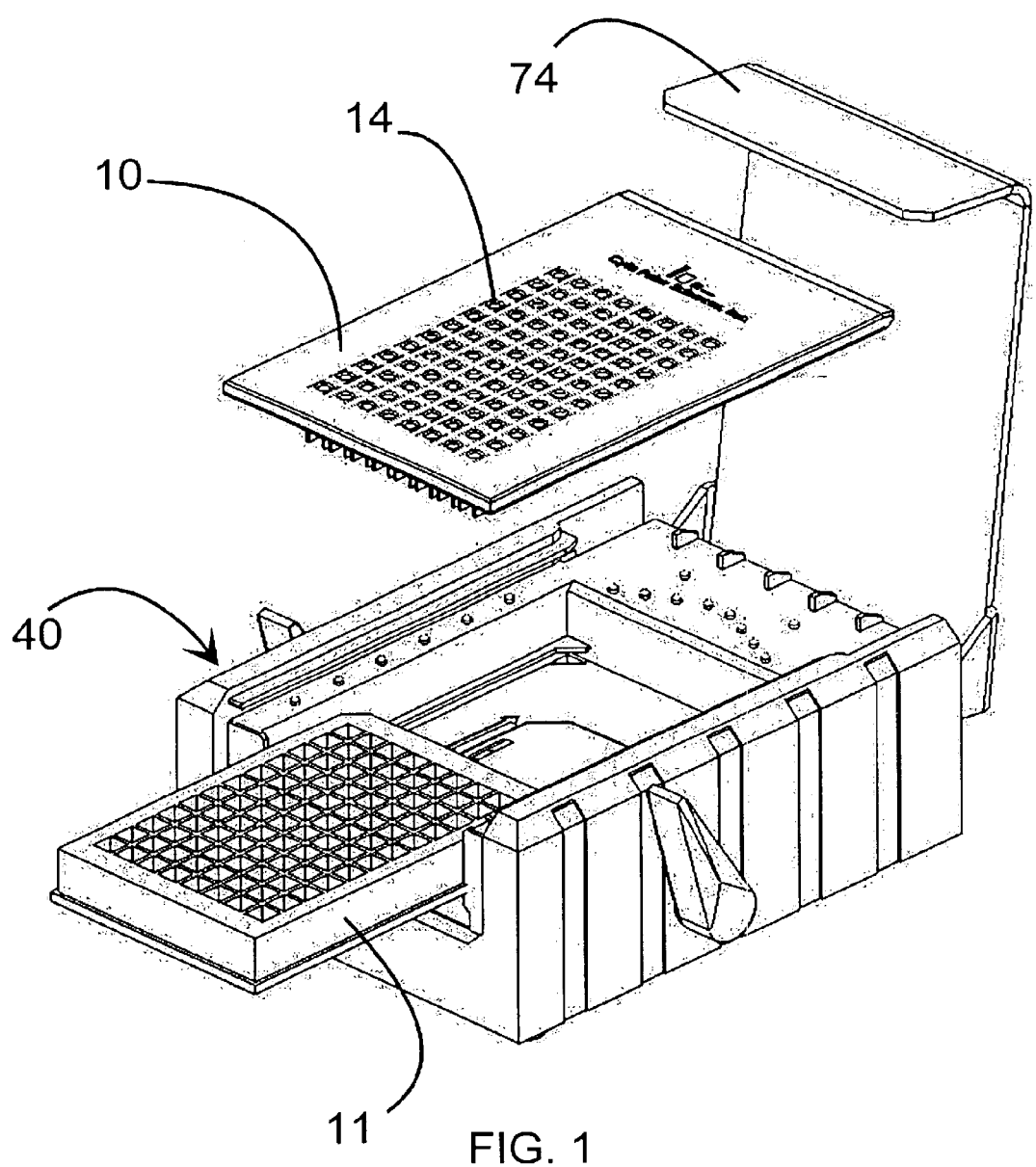
FIG. 1 is an exploded top perspective view of a multiple electrode pair array and a multiple well plate used with an embodiment of an apparatus for receiving and aligning a multiple electrode pair array and a multiple treatment cell used in electroporation, of the invention.
Figure 2:
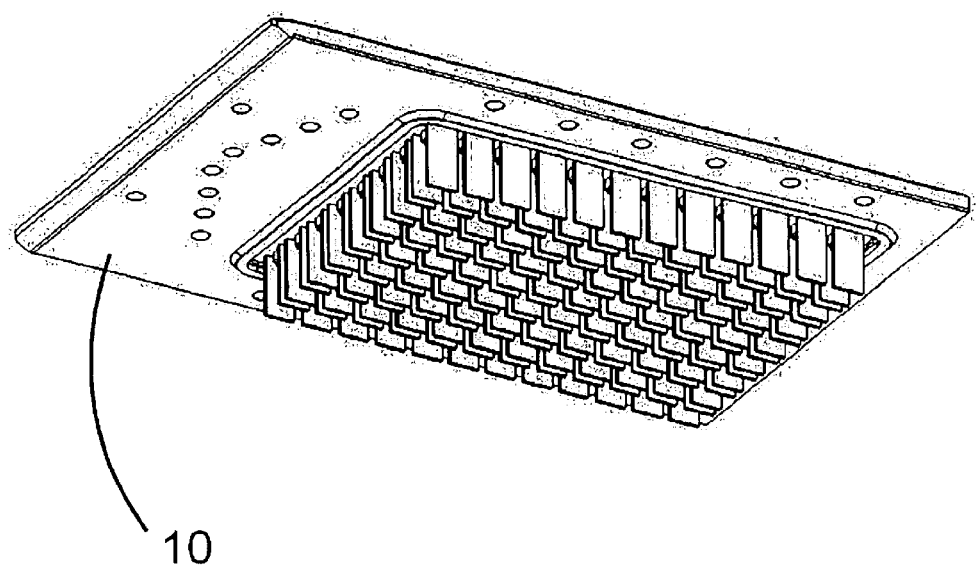
FIG. 2 is a bottom perspective view of the multiple electrode pair array apparatus shown in FIG. 1.
Figure 6:
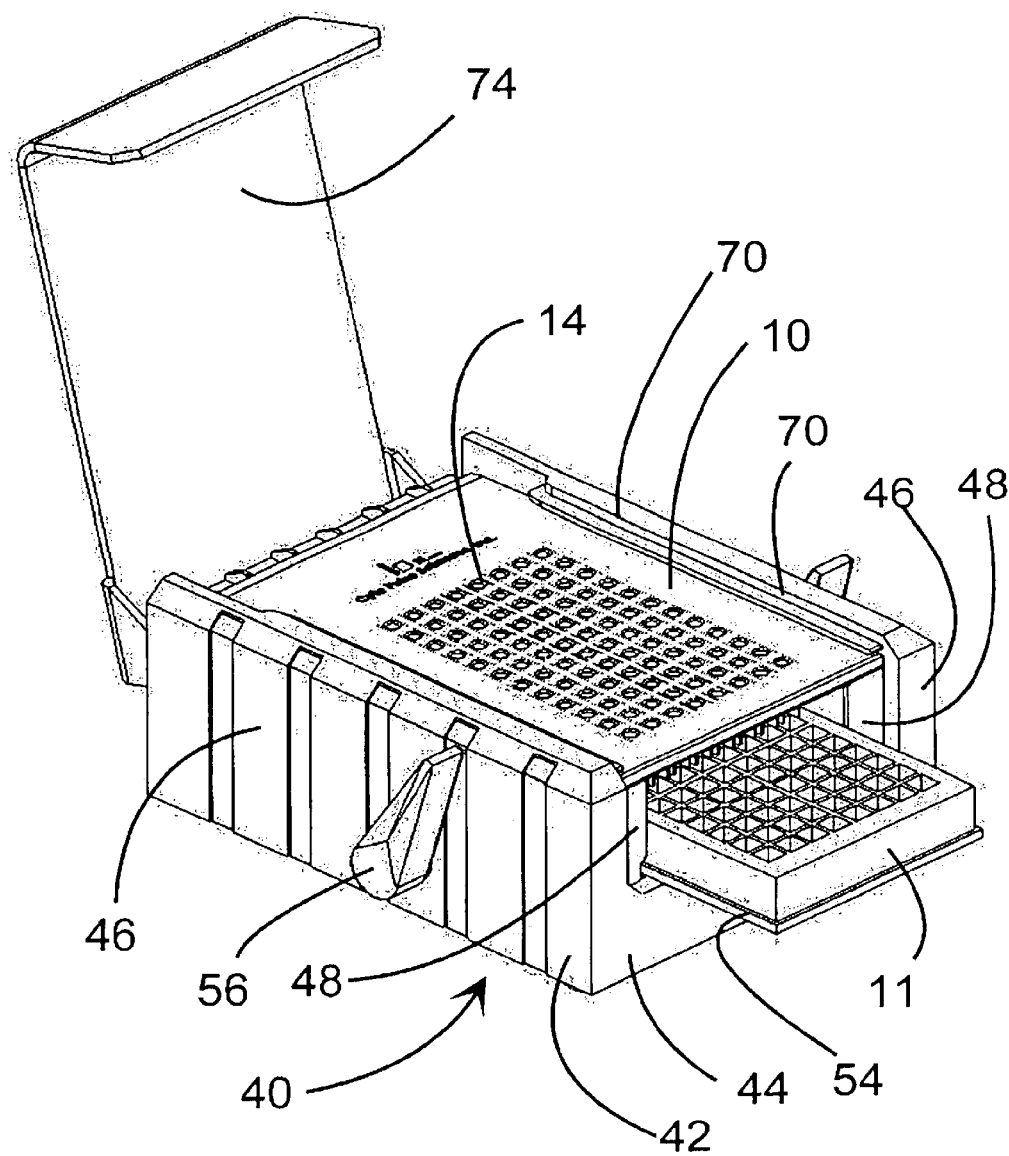
FIG. 6 is a perspective view of the embodiment of the invention shown in FIG. 1 wherein the multiple electrode pair array has been received on the subject apparatus, and wherein the multiple well plate is being slid into the subject apparatus.
Figure 7:
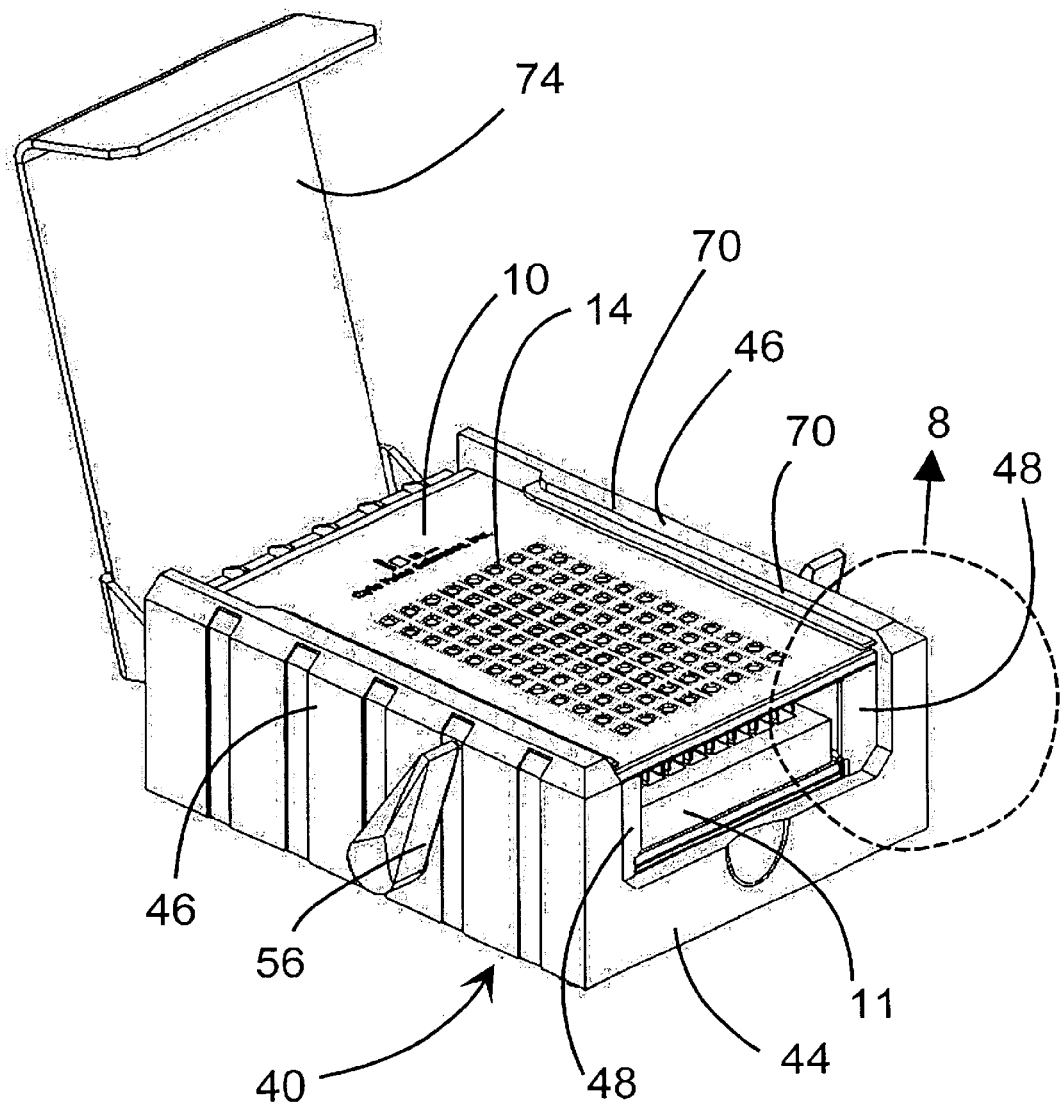
FIG. 7 is a perspective view of the embodiment of the invention shown in FIG. 6 wherein the multiple well plate has been completely slid into the subject apparatus.
Figure 8:
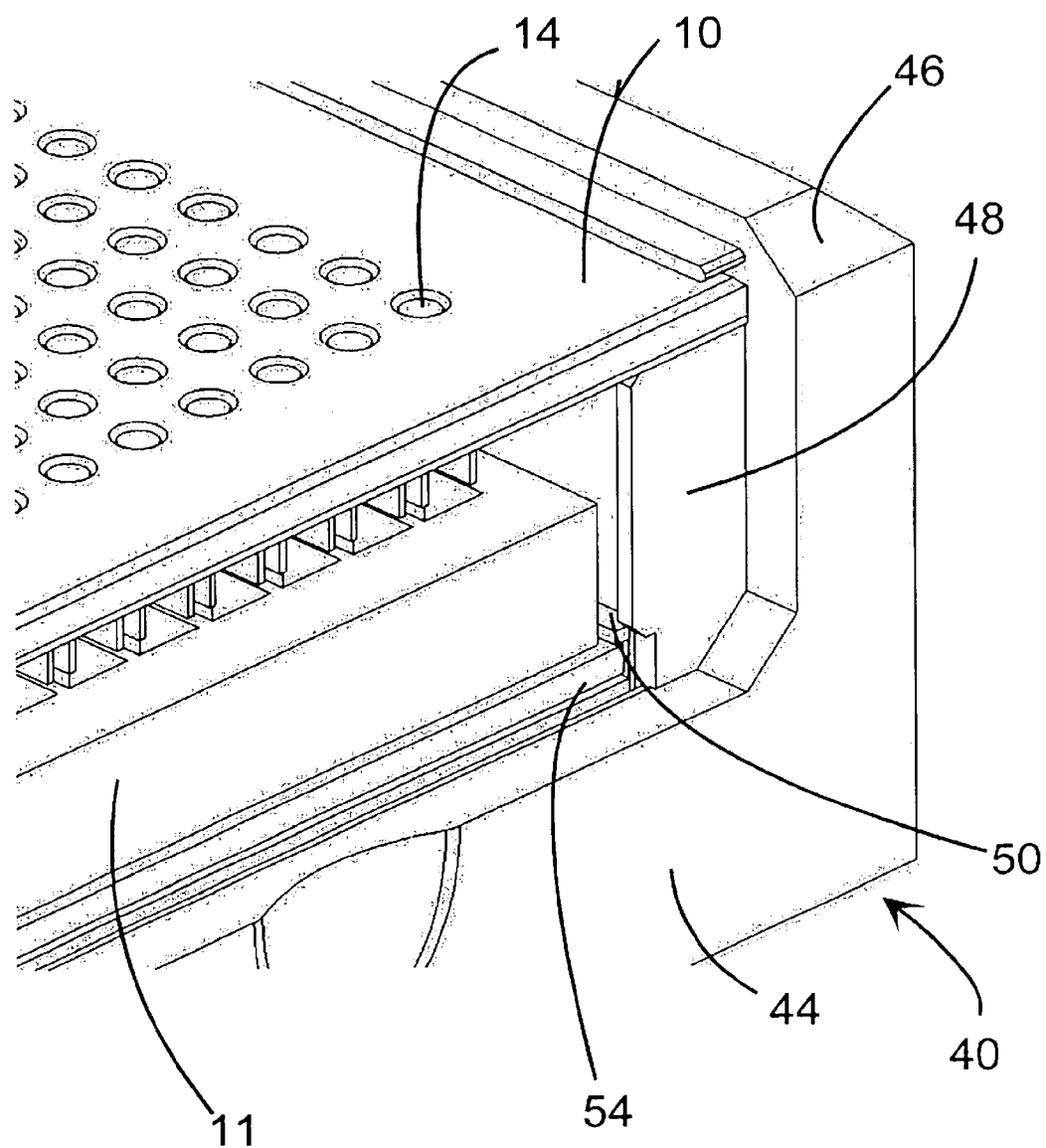
FIG. 8 is a partially enlarged view of the embodiment of the invention shown in FIG. 7 that is contained circled region 8 thereof of FIG. 7.
Figure 9:
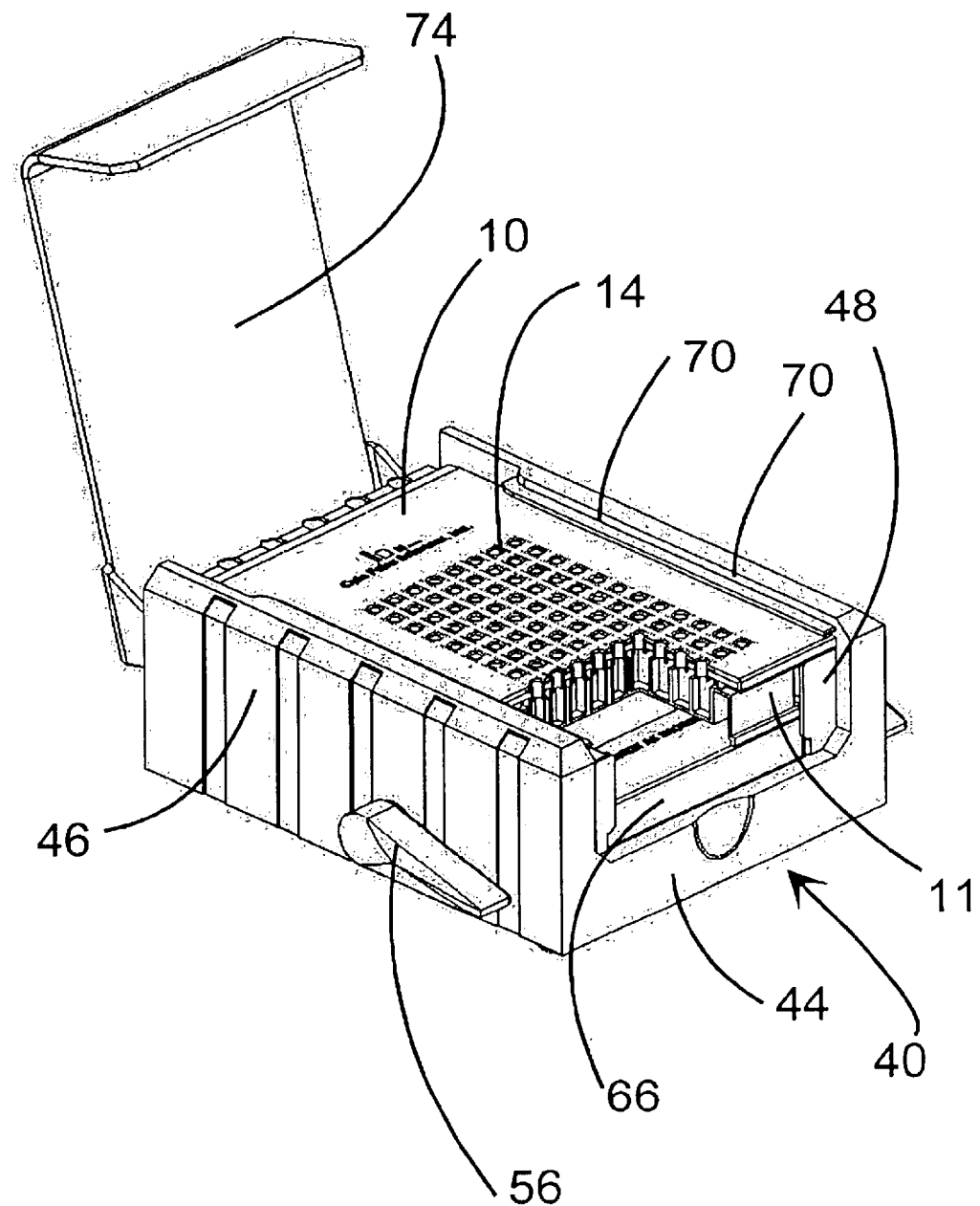
FIG. 9 is a partially broken away perspective view of the embodiment of the invention shown in FIG. 7 wherein the multiple well plate has been raised to be in engagement with the electrode pairs of the multiple electrode pair array.

Then, as shown in FIGS. 9 and 10, the lifting/lowering handles 56 are moved to their full extent in the clockwise direction. As a result, the respective pairs of electrodes in the multiple electrode pair array 10 enter the corresponding wells in the multiple well plate 11. In addition, respective inside walls 13 of the wells enter into respective adjacent electrode pair spacing gaps 28.

Once the respective electrode pairs in the multiple electrode pair array 10 are fully entered into the respective wells of the multiple well plate 11, solutions to be treated, such as by electroporation, can be added through the respective access channels 14 to the respective wells. Also, the row/column conductor plug 36 is connected to the socket assembly (not shown) on the apparatus for receiving and aligning a multiple electrode pair array and a multiple well plate 40, and the lid 74 is closed to bypass the disabling switch, e.g. interlock, (not shown).

Then, the contents of the respective wells can be subjected to treatment with respective electric field modalities. Using the multiple electrode pair array 10. Each well is individually addressable and individually treatable.

After treatment is complete, the lid 74 is lifted, thereby actuating the disabling switch, e.g. interlock, (not shown).

Then, the lifting/lowering handles 56 are rotated in a counterclockwise direction. When this occurs, referring to FIG. 11, the driving cam portion 60 of the offset axle 58 moves against the tray lowering cams 80. As a result, the plate lifting/lowering tray 66 and the multiple well plate 11 are lowered away from the multiple electrode pair array 10. Also, the plate lifting/lowering tray 66 moves clear of the hold-down-clip actuator arms 72, thereby permitting the hold-down clips 70 to move away from the multiple electrode pair array 10 and back into the side housing portions 46. When the lifting/lowering handles 56 are in their fully counterclockwise direction, the wells in the multiple well plate 11 are completely disengaged from the pairs of electrodes in the multiple electrode pair array 10, and the multiple electrode pair array 10 can be readily lifted off of the apparatus 40 for receiving and aligning a multiple electrode pair array 10 and a multiple well plate 11.

As mentioned hereinabove, the amount of frictional resistance to overcome to fit a 96 electrode pair matrix array into a conventional 96 well multiple well plate can be quite substantial. Conversely, there is a substantial amount of frictional resistance to overcome to remove a 96 electrode pair matrix array from a 96 well multiple well plate after it has been fitted into a 96 well multiple well plate.

With respect to these frictional considerations, there is a large mechanical advantage in the relatively large turning movement of the lifting/lowering handles 56 with respect to the relatively small vertical movement of the multiple well plate 11 toward and away from the multiple electrode pair array 10. Such large mechanical advantage allows these frictional forces to be readily overcome by manual operation of the lifting/lowering handles 56.

The apparatus for receiving and aligning a multiple electrode pair array and a multiple treatment cell used in electroporation 40 of the invention can be used as a stand alone unit, or it can be integrated into an automated robotics system.

Generally, the components of the multiple electrode pair array of the invention can be made from inexpensive and durable metal and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing an apparatus for receiving and aligning a multiple electrode pair array and a multiple well plate that is low in cost, relatively simple in design and operation, and which may advantageously be used to properly align and register a multiple electrode array with a multiple well plate. With the invention, an apparatus for receiving and aligning a multiple electrode pair array and a multiple well plate is provided which facilitates overcoming the frictional resistance for fitting a 96 electrode pair matrix array into a conventional 96 well multiple well plate. With the invention, an apparatus for receiving and aligning a multiple electrode pair array and a multiple well plate is provided which facilitates overcoming the frictional resistance for fitting a multiple electrode pair matrix array into a conventional multiple well plate. With the invention, an apparatus for receiving and aligning a multiple electrode pair array and a multiple well plate is provided which facilitates overcoming the frictional resistance to remove a 96 electrode pair matrix array from a conventional 96 well plate. With the invention, an apparatus for receiving and aligning a multiple electrode pair array and a multiple well plate is provided which facilitates overcoming the frictional resistance to remove a multiple electrode pair matrix array from a conventional multiple well plate. With the invention, an apparatus for receiving and aligning a multiple electrode pair array and a multiple well plate is provided which places pairs of rectangular electrodes into rectangular wells so that the rectangular electrodes closely fit against adjacent walls of the wells.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed is:

1. An apparatus for receiving and aligning a multiple electrode pair array and a multiple well plate used in electroporation, comprising:
    a housing which includes a bottom housing portion and a pair of side housing portions which project upward from said bottom housing portion,
    a pair of board-reception structures adjacent to said inner portions of said side housing portions, and
    multiple well plate engaging and disengaging means, supported by said housing, for engaging a multiple well plate with a multiple electrode pair array and for disengaging a multiple well plate from a multiple electrode pair array.

2. The apparatus of claim 1 wherein said multiple well plate engaging and disengaging means include a multiple well plate lifting and lowering assembly.

3. The apparatus of claim 2 wherein said multiple well plate lifting and lowering assembly includes:
    a lifting/lowering handle located outside said housing,
    an offset axle connected to said lifting/lowering handle, wherein said offset axle includes a driving cam portion,
    tray lift rods in contact with said driving cam portion of said offset axle, wherein said tray lift rods are connected to said bottom housing portion by lift-rod-retainer portions,
    a plate lifting/lowering tray in contact with said tray lift rods, wherein a bottom portion of said plate lifting/lowering tray includes a plurality of transverse force-balancing ribs, and
    tray lowering cams, connected to a bottom portion of said plate lifting/lowering tray, for engaging said offset axle for lowering said plate lifting/lowering tray.

4. The apparatus of claim 3, further including:
    a pair of well-plate alignment grooves connected to said plate lifting/lowering tray adjacent to said board-reception structures.

5. The apparatus of claim 3, further including:
    hold-down clips supported by said housing and actuated by movement of said plate lifting/lowering tray.

6. The apparatus of claim 5, further including:
    hold-down-clip actuator arms, operated by said plate lifting/lowering tray, for actuating said hold-down clips.

7. The apparatus of claim 1, further including:
    an inside alignment surface that is contacted by a complementary outside alignment surface on an outside corner of the multiple well plate.

8. The apparatus of claim 1, further including:
    a lid connected to said housing.

9. The apparatus of claim 8, further including:
    a pair of hinges for connecting said lid to said housing.

10. The apparatus of claim 1, further including:
    a socket assembly supported by said housing, wherein said socket assembly includes electrical conductors for contacting corresponding row electrical connection members and column electrical connection members on the multiple electrode pair array.

* * * * *